(12) United States Patent
Marcus et al.

(10) Patent No.: US 6,978,184 B1
(45) Date of Patent: Dec. 20, 2005

(54) OPTIMIZATION METHOD FOR CARDIAC RESYNCHRONIZATION THERAPY

(76) Inventors: Frank I. Marcus, 4949 E. Glenn, Tucson, AZ (US) 85712; Ding Sheng He, 377 Westford Rd., Tyngsboro, MA (US) 01879

( * ) Notice: Subject to any disclaimer, the term of this patent is extended or adjusted under 35 U.S.C. 154(b) by 90 days.

(21) Appl. No.: 10/629,881

(22) Filed: Jul. 29, 2003

Related U.S. Application Data (60) Provisional application No. 60/399,028, filed on Jul. 29, 2002.

(51) Int. Cl.[7] .............................................. A61N 1/05
(52) U.S. Cl. .................................................... 607/120
(58) Field of Search .................. 607/17, 120; 600/508, 600/514, 515, 519

(56) References Cited

U.S. PATENT DOCUMENTS 5,334,222 A * 8/1994 Salo et al. ..................... 607/17

* cited by examiner

Primary Examiner—George Manuel
(74) Attorney, Agent, or Firm—Gavin J. Milczarek-Desai; Quarles & Brady Streich & Lang LLP (57) ABSTRACT

The patterns of contraction and relaxation of the heart before and during left ventricular or biventricular pacing are analyzed and displayed in real time mode to assist physicians to screen patients for cardiac resynchronization therapy, to set the optimal A-V or right ventricle to left ventricle interval delay, and to select the site(s) of pacing that result in optimal cardiac performance. The system includes an accelerometer sensor; a programmable pace maker, a computer data analysis module, and may also include a 2D and 3D visual graphic display of analytic results, i.e. a Ventricular Contraction Map. A feedback network provides direction for optimal pacing leads placement. The method includes selecting a location to place the leads of a cardiac pacing device, collecting seismocardiographic (SCG) data corresponding to heart motion during paced beats of a patient's heart, determining hemodynamic and electrophysiological parameters based on the SCG data, repeating the preceding steps for another lead placement location, and selecting a lead placement location that provides the best cardiac performance by comparing the calculated hemodynamic and electrophysiological parameters for each different lead placement location.

23 Claims, 4 Drawing Sheets

OPTIMIZATION METHOD FOR CARDIAC RESYNCHRONIZATION THERAPY

CROSS REFERENCE TO RELATED APPLICATION

This application claims priority to U.S. Provisional Patent Application Ser. No. 60/399,028, which was filed on Jul. 29, 2002 by the same inventors.

BACKGROUND OF INVENTION

1. Field of Invention

The present invention relates generally to the implantation of a cardiac pacing device used for cardiac resynchronization therapy (CRT). More specifically, the present invention relates to a realtime method for CRT candidate screening, for optimizing the placement of one or more leads, and for determining optimal settings for cardiac pacing devices.

2. Description of Related Art

Heart failure afflicts about twenty-five million people worldwide, with about two million new cases diagnosed each year. In the United States, hospitalization for heart failure amounts to more than 6.8 million days a year, and the total cost of treatment is more than $38 billion annually, which is increasing as the population ages. The prevalence of congestive cardiac failure is also increasing due to improved survival from both myocardial infarction and hypertension that has resulted from the use of drug therapies, such as angiotension-coverting enzyme inhibitors, beta-blockers, and digoxin. Nevertheless, many patients remain markedly symptomatic despite maximal medical therapy. Furthermore, patients with left ventricular failure are at an increased risk of progressive heart failure or sudden death.

In some heart patients, congestive cardiac failure affects the synchronous beating of the ventricles. Accordingly, the left ventricle is not able to pump blood efficiently to supply the body with needed oxygen and nutrients. In approximately 30% of patients with heart failure, an abnormality in the heart's electrical conduction system, called an intraventricular conduction delay or bundle branch block, causes the left ventricle to beat in an asynchronous fashion. This greatly reduces the efficiency of the left ventricle in patients whose hearts are already damaged. In addition, the right and left ventricles begin to beat slightly out of phase instead of beating simultaneously.

A significant minority of patients with congestive heart failure have marked prolongation of the QRS complex of their electrocardiographic (ECG) profile, which represents the time it takes for the depolarization of the ventricles. The prolongation is an indicator of intraventricular conduction abnormality and is associated with decreased left ventricular systolic function. The development of new QRS prolongation is associated with reduced left ventricular function.

Normally, electrical activation is conducted by the His bundle and Purkinje system, and an impulse spreads transmurally from the septum to multiple paraseptal regions resulting in synchronous contraction of the ventricles. Many patients with heart failure have poor electrical conduction in the heart that results in a pattern called left bundle branch block (LBBB) or intraventricular conduction delay. In these patients, the duration of the QRS complex may exceed 130 milliseconds (ms) compared with a normal duration of less than 100 ms. In LBBB, the left ventricle is activated belatedly throughout the septum from the right ventricle, with anteroseptal crossing preceding inferioseptal crossing. The latest activation is in the posterior inferior aspect of the left ventricle, often remote from the base.

Additionally in patients with LBBB, the delay between the onset of left and right ventricle systole may be prolonged to 85 ms resulting in significantly later aortic opening, aortic valve closure, and mitral valve opening. LBBB does not affect the timing of right ventricle events, and the delay in the left ventricle events leads to a reversal of the usual sequence of right and left ventricle systole. In addition, the range of isovolumic contraction times in patients with LBBB is wide (20–100 ms), suggesting heterogeneity of left ventricle activation. The delay in aortic valve closure leads to a relative decrease in the duration of left ventricle diastole. In patients with LBBB, prolonged depolarization or abnormal depolarization may result in regional myocardial contraction into early diastole, causing a delay of mitral valve opening with prolongation of left ventricle isovolumic relaxation time of up to 300% and shortened left ventricle filling time. LBBB is also associated with abnormal diastolic function on Doppler echocardiography examination. Further, left ventricle intraventricular conduction delay may add significantly to dyssynchrony, particularly in ischemic heart disease.

In patients with an intraventricular conduction defect or with LBBB, cardiac resynchronization therapy (CRT) shortens the duration of the QRS complex and has been shown to improve the patient's symptoms markedly. CRT is the use of a specialized pacemaker to improve contraction coordination of the left ventricle. The specialized pacemaker may also be programmed to coordinate the beating of the two ventricles by pacing the left ventricle individually to match the beating of the right ventricle or both ventricles simultaneously. It has been shown that resynchronization of abnormal intraventricular and interventricular asynchrony with left ventricular or biventricular pacing may symptomatically improve patients with severe ventricular failure. While the results have been positive, most studies have shown that approximately 30% of patients do not obtain any measurable benefit from the therapy. It is now being tested to see if this therapy will increase the duration of life.

In biventricular pacing, one wire or catheter is implanted in the right ventricle and another is threaded into a vein, the coronary sinus, which drains into the right atrium to pace the left ventricle. The coronary sinus catheter is then guided to the lateral or posterior part of the left ventricle. Alternatively, a left ventricular lead can be implanted by thoracotomy (i.e., through a small incision between the ribs, the lead is implanted on the surface of the left ventricle) or even by crossing the atrial septum and inserting the lead inside the left ventricle. Yet, the exact and best position for each catheter position is difficult to determine at the time of insertion. In fact, there are no physiological means to determine the best site at the time of lead placement except possibly the use of echocardiography, which is time consuming and poses a problem in keeping the operative field sterile.

In addition, it is difficult to predict the effectiveness of CRT before the insertion of the cardiac pacing device. Currently, physicians often measure a decrease in QRS duration after biventricular pacing to evaluate CRT. However, the decrease in the QRS duration does not correlate well with the improvement of cardiac function in some patients. Other parameters have been also used to determine the effectiveness of CRT, such as improvement of New York Heart Association (NYHA) classification score, six-minute hall walk results, etc. However, these parameters cannot be evaluated in real time and do not provide information that physicians need to know at the time of lead and device implantation to determine if the patient will benefit from CRT. Finally, it is not clear if one lead implanted into the coronary sinus is as good as two leads implanted into the right and left ventricles.

Another problem encountered, particularly with the use of dual-chamber pacemakers, is the proper setting of the so-called "A-V delay interval." Basically, the A-V delay interval refers to the time interval between a ventricular stimulation pulse and a preceding atrial depolarization. Because the sequence of atrial and ventricular pacing is vital to the efficiency of the heart as a pump, a non-optimal A-V delay interval can seriously impact heart performance. Indeed, relatively small departures from the optimal A-V delay interval value can greatly reduce the hemodynamic contribution of the atria in patients with congestive heart failure.

At present, physicians select and program the A-V delay interval empirically. Since the hemodynamic contribution of the atrial depolarization to cardiac output is well known, every effort is made to select the optimal A-V delay interval for a given patient. However, the optimal A-V delay value can vary over time as the patient ages or the disease state changes.

Therefore, there is a need for a way to provide a reliable prediction for whether a patient would be a good candidate for cardiac resynchronization therapy, for a way to determine the optimal placement of leads of a cardiac pacing device in realtime while the pacing device is implanted into the patient, and for a way to optimize the selection of the A-V delay interval, both during the initial placement of a dual-chamber pacemaker and during follow-up evaluations.

SUMMARY OF INVENTION

The invention generally relates to a realtime method for CRT candidate screening, for optimizing the placement of pacemaker leads, and for determining optimal settings for cardiac pacing devices. The system of the invention includes an accelerometer sensor, a programmable pace maker or other means for stimulating heart pacing, a computer data analysis module, and a 2D and 3D visual graphic display of analytic results, i.e., a ventricular contraction map. The method includes placing the leads of a cardiac pacing device, collecting seismocardiographic (SCG) data corresponding to heart motion during both normal (i.e., unpaced) conduction and during paced beats of a patient's heart, determining hemodynamic parameters based on the SCG data, and using this data to screen patients for CRT and to determine optimal lead placement.

Accordingly, a main objective of the present invention is to determine if a patient is an appropriate candidate for resynchronization therapy in realtime during an electrophysiology study.

An additional objective of the present invention is to determine the optimal site(s) of lead implantation for cardiac resynchronization therapy, and, therefore, enhance the effectiveness of the therapy.

Another objective of the present invention is to determine if the patient needs only the left ventricular pacing instead of biventricular pacing in realtime during an electrophysiology study.

According to the preferred embodiment, an accelerometer placed over a patient's chest at the time of insertion of pacing leads can help identify the optimal site. A computer algorithm processes the seismocardiographic measurements and generates a ventricular contraction mapping, which displays the rate of pre-ejection and ejection, the duration of the pre-ejection period, duration of systole, and duration of isovolumic relaxation period. Examining changes in the relevant data at different lead locations results in the determination of the best site of lead placement. For example, indicative behavior includes a shortening of the pre-ejection period, and an increase in the rate of contraction of the left ventricle. Additionally, the degree of mitral valve regurgitation, which alters the patterns of chest wall motion, should markedly decrease with the optimal site.

It is possible that accelerometer patterns will help identify patients who would be likely to benefit from CRT by showing a recognizable pattern of minimal desynchronization (in which case CRT would not be beneficial) or marked desynchronization (in which case CRT would be most helpful).

Thus, the invention may be used during an electrophysiology study (EPS) to help determine if CRT is an effective treatment for a particular patient. During an EPS, catheters are placed in the heart and electrically stimulate different areas to identify abnormalities in the heart's conductive system. According to the present invention, an accelerometer measures the seismocardiographic behavior at different stimulation locations. The resulting data is analyzed to determine whether the patient only needs left ventricular or biventricular pacing or if CRT would be beneficial at all. If CRT is found to be an effective treatment, the cardiac pacing device could be implanted during the same procedure with the leads placed at an optimal location. Since one third of patients who have left ventricular or biventricular pacing do not improve with this procedure, the accelerometer-guided ventricular pacing could diminish this high incidence of ineffectiveness. Thus, the method and system of the invention can provide reliable prediction whether the patients would be candidates for CRT as well as provide optimal location for pacing lead placement during the implantation. Also, optimal settings for delay between onset of right and left ventricular contraction could be determined.

Furthermore, the method of the invention may be used to select an optimal A-V delay interval for a patient based on comparing an index of cardiac performance for several delay intervals. In a preferred embodiment, various candidate A-V delay intervals and pacing rates are programmed into the pacemaker and realtime seismocardiographic (SCG) data and electrocardiographic (ECG) data are collected. The collected data is processed to develop a canonical SCG waveform. Next, certain features in the SCG waveform are identified and used to determine time intervals between the atrial depolarization and ventricular stimulation pulse events. This time interval information is used to define an index of cardiac performance that can be compared with other indices representing several different pacemaker A-V delay intervals.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

DETAILED DESCRIPTION OF THE PREFERRED EMBODIMENTS

The invention relates in general to a method for providing a reliable prediction for whether a patient would be a good candidate for cardiac resynchronization therapy and for determining the optimal placement of leads and settings of a cardiac pacing device in real time while the pacing device is implanted into the patient. In one embodiment, the method of the invention preferably includes detecting hemodynamic parameters corresponding to the motion of a patient's heart with an accelerometer, converting the detected parameters into digital data that is fed into an analysis module for calculation and display of ventricular contraction mapping, and comparing the results generated by different pacemaker lead placement to provide an optimal lead location. In another embodiment, hemodynamic parameters are detected and compared to those generated by an unpaced heart, thereby predicting whether CRT is an appropriate option for a given patient.

The invention further relates to a method for selecting an A-V delay interval for a pacemaker patient that includes the steps of selecting and setting an initial A-V delay value, collecting SCG data corresponding to heart motion during paced beats of the patient's heart, locating the mitral valve closure point, the atrial valve opening point, and the atrial valve closing point in the SCG data, calculating the time interval between the aforementioned points, computing an index of cardiac performance based on the aforementioned points, and selecting the A-V delay value that optimizes the index of cardiac performance.

Figure 2:
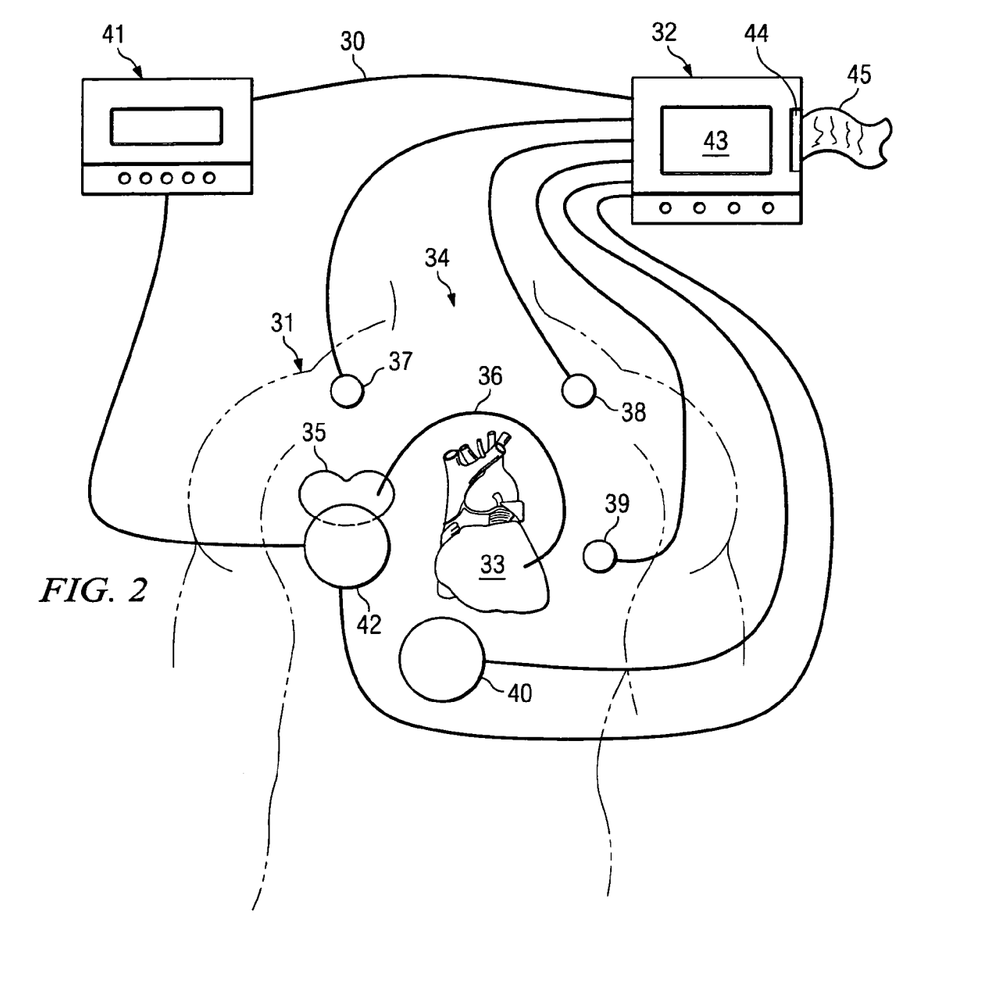
FIG. 2 is a schematic depiction of an SCG/ECG analysis system and pacemaker lead placement test system connected to wires or catheters inside a patient.

FIG. 2 is a schematic diagram representing the various connections between the pacemaker patient 31, the pacemaker programmer 41, and the SCG/ECG analysis system 32. The drawing shows a dual chamber pacemaker 35 implanted in the pacemaker patient 31 and coupled to the patient's heart 33 through a suitable lead 36. Although one lead is shown, it should be recognized that pacemakers having more than one lead may be used with the invention (for example, a pacemaker with an atrial lead and one or more a ventricle leads). The pacemaker programmer 41 communicates with the implanted pacemaker 35 through a programming head 42 shown in position over the pacemaker 35 implant site. The pacemaker programmer 41 can be used to alter the A-V delay interval, the right ventricle to left ventricle delay, pacing rate, and pacing mode of the implanted pacemaker 35 via telemetry.

The SCG/ECG system 32 is coupled to the pacemaker patient 31 and used to collect realtime ECG data from an array of surface electrodes 37, 38, and 39 which are placed upon the patient's chest 34. The surface ECG reflects both the electrical activity arising from the patient's heart 33 and the pacing artifacts arising from the pacemaker 35. The SCG/ECG system 32 can detect and distinguish both sensed and paced cardiac events. Paced cardiac events typically generate a narrow pulse artifact on the surface ECG of the patient. Pacing may also cause inversion of the associated physiologic wave form. Therefore, it is preferred to use ECG "QRS" detection algorithms that recognize narrow pacing artifacts and that recognize negative going and positive going physiologic wave forms. While any of a variety of well known techniques can be used to achieve this result, it is preferred to discriminate the atrial and ventricular pacing artifacts based upon their high slew rate and to recognize physiologic wave forms based upon the absolute value of their amplitudes rather than the sign of their amplitudes.

The SCG/ECG system 32 may be coupled to the pacemaker programmer 41 through a data link 30, which permits the system 32 to receive marker channel diagnostic telemetry from the implanted pacemaker 35. Diagnostic telemetry permits the pacemaker programmer 41 to access near real-time sensing and pacing information from the implanted pacemaker 35. Examples of such cardiac events include the occurrence of atrial events, both sense (AS) and pace (AP), and ventricular events, both sense (VS) and pace (VP).

The SCG/ECG system 32 also collects realtime SCG data from a suitable seismic sensor 40, which is placed upon the patient's chest 34. The seismocardiogram reflects accelerations of the patient's heart 33 walls during the cardiac cycle. The SCG/ECG system 32 evaluates this input data and presents canonical wave forms and other output data on a video display 43 and on a printer 44.

Suitable SCG/ECG systems 32 for carrying out the invention are manufactured by Bard Electrophysiology of Lowell, Mass., GE Medical Systems, or EPMED. The preferred instrument is a multiple-channel electophysiological recording and analysis system that can acquire physiological signals, i.e., surface and intracardiac electrograms, hemodynamic data (e.g., arterial blood pressure), as well as fluoroscopic, ultrasound, MIR and/or CT images. These signals could be acquired in both analog and digital format. The SCG signal would be acquired by the accelerometer and fed into the physiological system. The SCG signal would then be processed by special computer algorithm and a series of hemodynamic and electrophysiological parameters would be generated or interpolated. For example, the patient's dp/dt (the rate of change of the ventricular pressure) and ejection fraction (EF, an indication of the ventricular function), etc. can be determined. Essentially, one can calculate the dp/dt from a SCG signal of the left ventricular pressure curve during the contraction using previously developed algorithms. For the EF, a value could be interpolated.

Thus, to evaluate the effectiveness of pacing and assess the optimal leads placement, baseline SCG parameters would be collected and analyzed. Then the SCG parameters collected during pacing at the testing sites would be collected and analyzed. The change of those key parameters will be served as a Stoke Index to determine the optimal pacing site and/or settings (e.g., A-V or right ventricle to left ventricle interval delay).

In addition, realtime baseline SCG parameters, i.e. PEP, LVET, PEP/LVET, also could be displayed and analyzed. The realtime data could be stored as a template for comparisons later. Then the set of realtime-time SCG parameters could be collected and compared with the template and the changes of those parameters and the correlation coefficient, r, could be generated. Based on the magnitude of the changes of the SCG parameters and the correlation coefficient, the optimal site of the leads placement could be determined.

Figure 3:
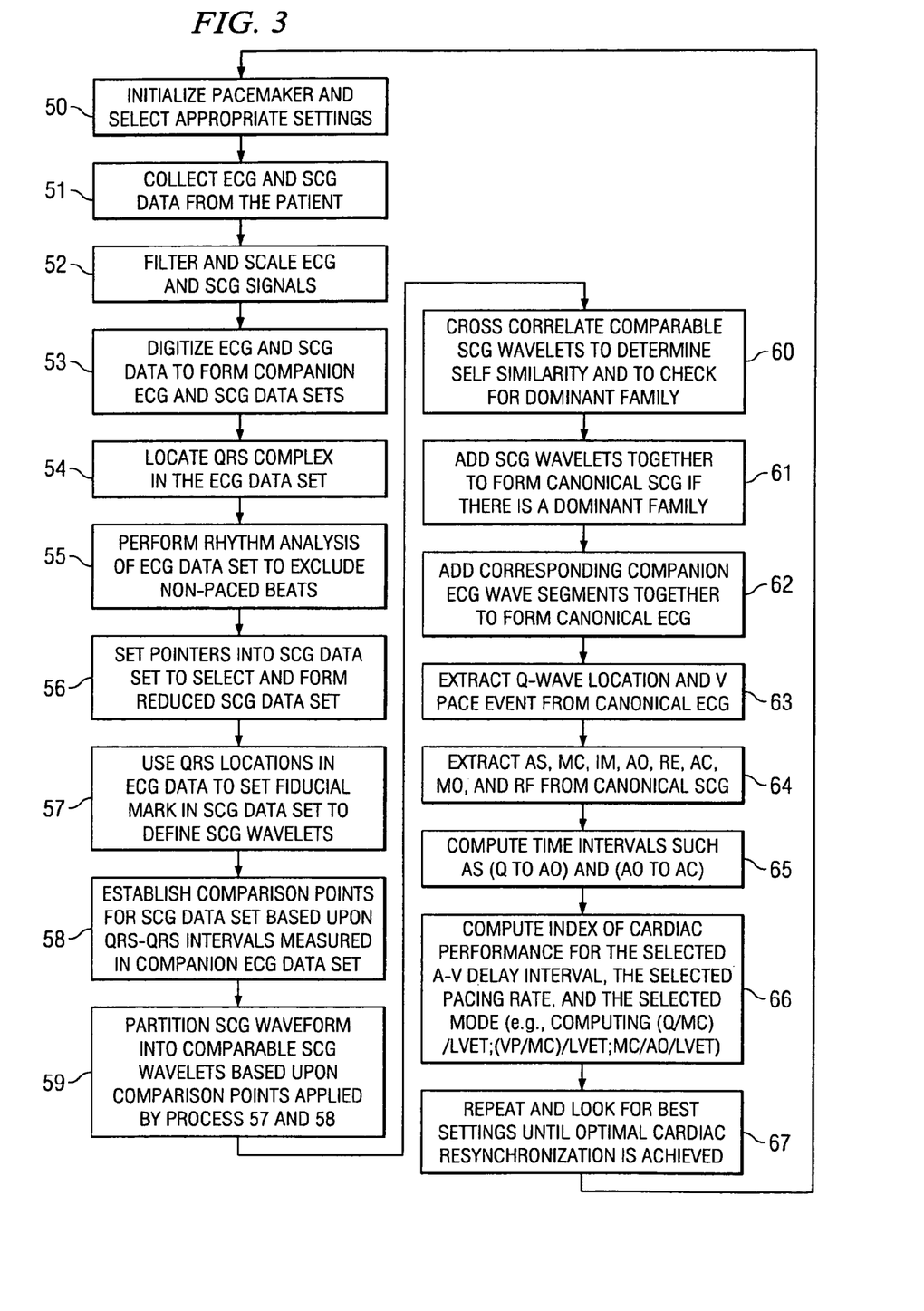
FIG. 3 is a flow chart illustrating the method used to collect and analyze the ECG and SCG waveforms in FIG. 1. Abbreviations are defined in the Detailed Description.

Any apparatus capable of carrying out the process of the invention may be used. An example of how the method of the invention can be practiced is shown in FIG. 3.

Process 50 involves initializing the pacemaker and requires selection of an initial candidate A-V delay interval. It is preferred to have this value and subsequent values set by a physician through the use of a pacemaker programmer 41. However, process 50 may be performed automatically by the pacemaker, or invoked by the SCG/ECG system through the data link 30.

The preferred method for carrying out process 50 is illustrated in the pacemaker marker channel telemetry wave form 10 (FIG. 1), which shows A-V sequential pacing (DVI) of the patient's heart at a rate above the patient's intrinsic rate. The V-V lower rate escape interval 19 selected for the patient and the A-V delay interval 18 are shown in the telemetry wave form 11. Consecutive lower rate escapes result in a sequence of paced beats depicted in the telemetry wave form 10, while the response of the heart 33 to this pacing regime is shown in the canonical ECG wave form 12. The corresponding motion of the heart is depicted in the canonical SCG wave form 14, while the corresponding state of the heart valves are set forth in the heart pictograph panel 16.

More specifically, an initial atrial pace (AP) event is shown as atrial pace event 13 in wave form 12 and as atrial pace event 11 in wave form 10. The atrial sequential pacing regime also gives rise to the ventricular pace event (VP) shown in wave form 12 as ventricular pace event 15 and shown in wave form 10 as ventricular pace event 17. This ventricular pace event occurs after the programmed A-V delay interval 18 shown in the telemetry wave form 10. A second set of atrial pace events 20 and 22 are shown with corresponding ventricular pace events 21 and 23 in FIG. 1.

Although the pacing modality and range of pacing rates may be varied, the purpose of this process 50 is to generate a sequence of ventricularly paced events. Preferred pacing rates range from about 60 bpm to about 115 bpm (that latter rate would be appropriate during exercise). For each given pacing rate, the A-V delay interval 18 may be varied from a nominal minimum value of less than about 100 ms to a nominal maximum value of approximately 250 ms. As would be recognized by one skilled in the art, the pacing rate must be faster than the intrinsic heart rate of the patient. Otherwise, one sees no paced beats if the pacemaker is set in inhibited mode or some beats if it is not. Also, the pacemaker may be set to pace the atrium, but with a shorter A-V delay than normal for the patient so that the ventricles are paced and captured.

Process 51 represents the collection of realtime ECG data from the electrode array 37, 38, 39 and the collection of realtime SCG data from the seismic sensor 40. After appropriate isolation, these real time signals are bandpass filtered in process 52 to eliminate noise. The filtering and scaling functions of process 52 may be carried out in analog hardware as taught by the incorporated references or in the digital domain by a dedicated processor or other software forming a part of the SCG/ECG instrument 32. It has been determined that the low frequency cutoff is the most important bandpass characteristic for the realtime signals and the lowest possible low frequency corner is preferred for both ECG and SCG signals.

Process 53 completes digitization of the ECG and SCG realtime signals and generates a pair of data sets, referred to as the SCG data set and the ECG data set. The temporal relationship between these two data sets is preserved during processing and the SCG data and ECG data sets may by considered "companions." Typically, subsequent software processes will generate pointers from the ECG data set to point into the companion SCG data set to collect segments of the companion SCG data for further analysis.

In process 54, the ECG data set is analyzed to find the location of the QRS complexes. The algorithm must detect naturally occurring depolarization as well as paced complexes from unipolar and bipolar pacers. At present, the preferred detection rule looks for the high amplitude rapid rise time pacemaker artifact to identify ventricular and atrial paced events, although other detection techniques may be freely substituted without departing from the scope of the invention. The principle purpose of this process is to find the QRS reference point to facilitate further analysis of the SCG data.

In optional process 55, a rhythm analysis is performed on the ECG data set based upon the locations of the QRS complexes in the ECG data. The primary purpose of the rhythm analysis of the ECG data is to exclude those segments of the companion SCG data from further processing which arise from electrically abnormal heart beats. This process is skewed toward over exclusion of beats to prevent corruption of the canonical SCG wave form. Reference may be had to the incorporated references for details on a suitable exclusion rhythm analysis process. However, it should be understood that there is great flexibility in carrying out this process. Also, many patients do not exhibit premature ventricular beats (PVCs) when paced above their intrinsic rate. This step may be used optionally, and the exemplary data shown in FIG. 4 was not submitted to rhythm analysis.

In optional process 56, the rhythm analysis of process 55 is used to point into the companion SCG data set to select segments of the companion SCG data for further processing. The selected SCG data is referred to as the "reduced SCG data set." The primary purpose of this optional process is to exclude non-sinus, non-paced beats from further analysis, because such data would otherwise frustrate the development of the canonical SCG.

In process 57, the location of the QRS complex is used to define a set of fiducial points which are transferred into the SCG data set. These fiducial points are used to break the SCG data into "wavelets."

In process 58, the instantaneous heart rate is used to define a set number of comparison points and to define a comparison window. It is preferred to set the comparison window to eighty percent of this measured heart rate interval, and to use approximately one hundred comparison points.

In process 59, the SCG data set is broken into comparable wavelets by applying the comparison points defined in process 58 about the fiducial points defined in process 57. In general, the fiducial point defines the origin for the distribution of the set of comparison points. It is preferred to distribute twenty percent of the comparison points to the SCG data collected prior to the QRS fiducial point and to apply eighty percent of the comparison points to the SCG data set collected after the QRS fiducial point. The application of comparison points in this process permits SCG wavelets recorded at different heart rates to be compared to each other without introducing rate induced distortions in the SCG morphology. The purpose of this process is to segment the SCG data set into comparable wavelets for subsequent cross-correlation.

In process 60, the individual wavelets are cross-correlated to ascertain the degree of similarity. Each wavelet is sequentially compared with all other wavelets. Those wavelets with a correlation coefficient of 0.9 or greater are grouped into one family. At the conclusion of the iterative cross-correlation, there is typically one dominant family with usually ninety percent or more of all the wavelets. If a dominant family of highly self-similar wavelets emerges, it is presumed that preceding processes have eliminated bad data from the analysis.

Figure 1:
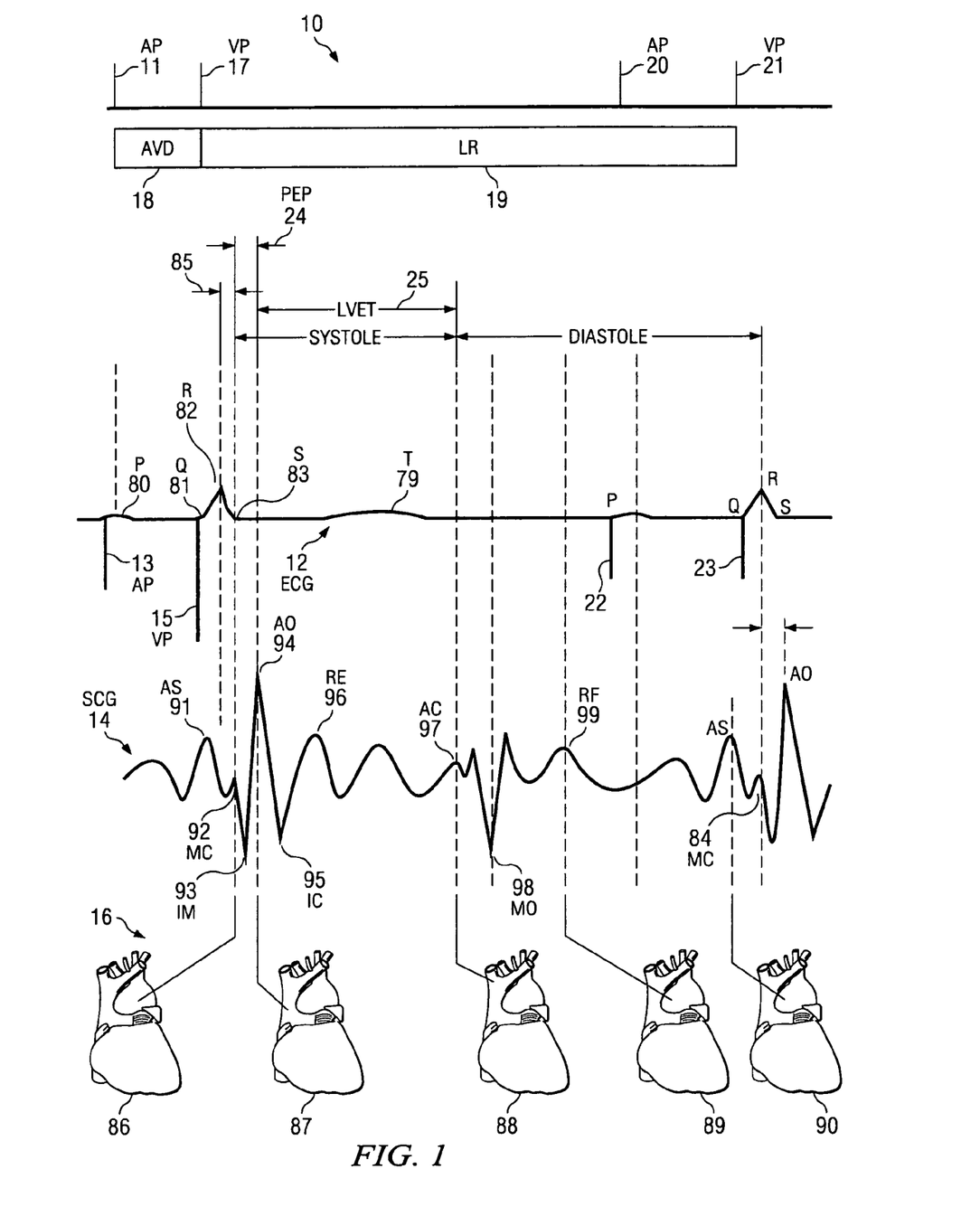
FIG. 1 is a schematic diagram depicting the relationship between pacemaker events, electrocardiogram (ECG) events, seismocardiographic (SCG) events, and the physical motion of the heart.
Figure 4:
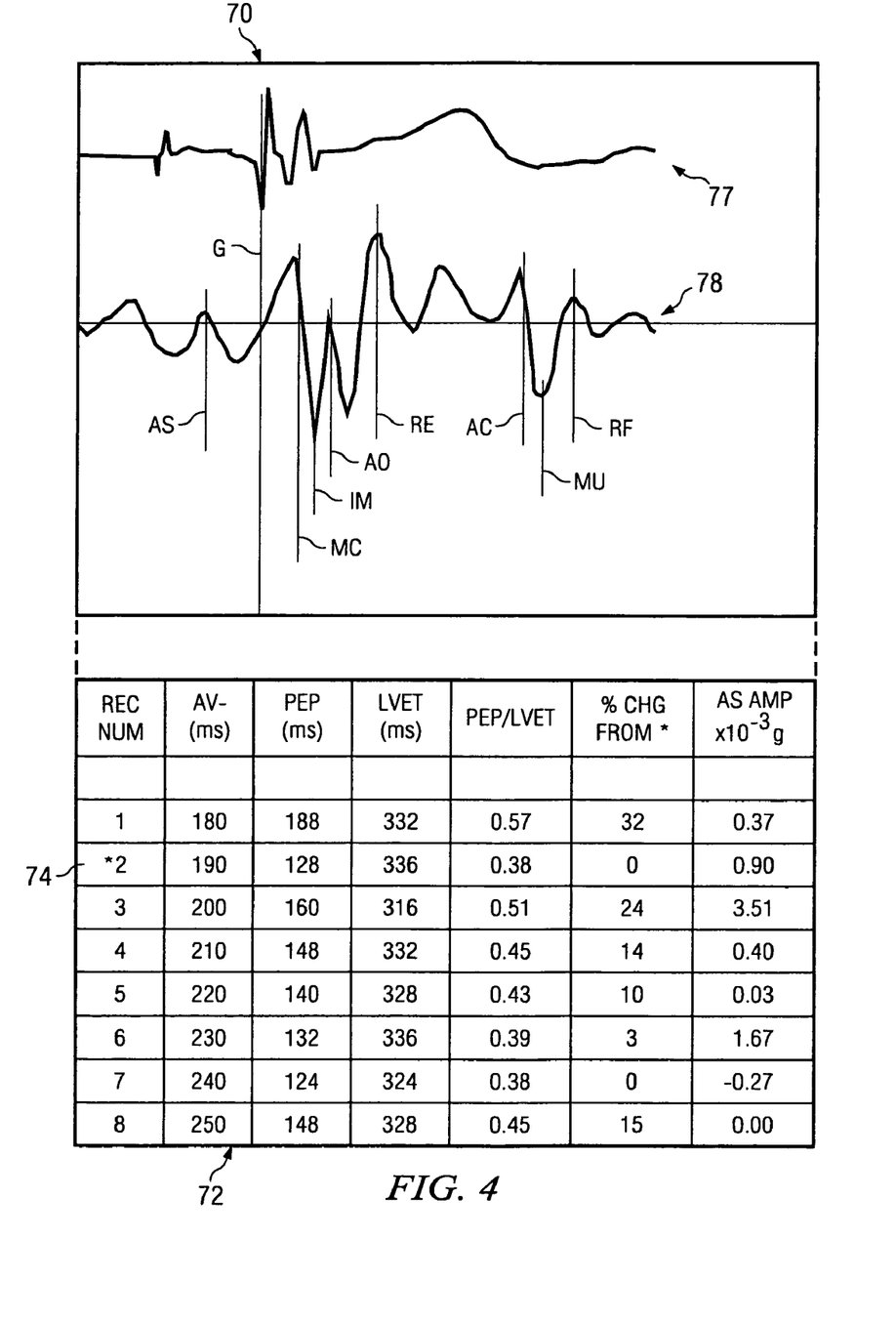
FIG. 4 is a partial screen display generated by the SCG/ECG analysis system.

In process 62, the corresponding and complimentary or companion ECG data are also added or averaged together to form a canonical ECG wave form shown in FIG. 1 as wave form 12 and in FIG. 4 as wave form 77. Thus, FIG. 1 and FIG. 4 represent processed data and is not a representation of any particular realtime wave forms.

In process 63, certain events are extracted from the canonical ECG data set. Referring back to FIG. 1, the underlying electrical events in the heart give rise to certain repetitive features which can be identified in the surface ECG shown as the canonical wave form 12. The atrial paced event 13 gives rise to the atrial depolarization of the heart shown as "P-wave" 80 in wave form 12. The subsequent ventricular paced event 15 generates the QRS complex, which includes the Q-wave 81, the R-wave 82, and the S-wave 83. The repolarization of the ventricular tissues give rise to the T-wave 79 feature in the wave form 12. A morphology detection algorithm is applied to the ECG data set to extract the R-wave 82 and the pacing spike associated with ventricular paced event 15. Peak/valley decision rules are applied to the digitized ECG data set. This "reduced data set" is evaluated for both the Q-wave and T-wave locations for individual heart beat cycles. The location of the Q-wave 81, and the (VP) ventricular paced event 15 are used in the subsequent resynchronization process, but addition events may be useful for further analysis of the canonical SCG waveform.

In process 64, certain repetitive features from the SCG recording are extracted. These events are identified on FIG. 1 by two-letter codes as follows: AS (atrial systole) event 91, MC (mitral closure) event 92, IM (isometric contraction) event 93, AO (aortic opening) event 94, RE (rapid emptying) event 96, AC (aortic closure) event 97, MO (mitral opening) event 98, and RF (rapid filling) event 99. These features of the canonical SCG wave form 14 have been related to underlying mechanical motions of the heart. The AS event corresponds to peak atrial systole as shown by heart pictograph 90. The AO event 94 corresponds to the opening of the aortic valve as seen in heart pictograph 87. The AC event 97 corresponds to the aortic valve closure as seen in heart pictograph 88. The MC event 92 correspond to the mitral valve closure as seen in heart pictograph 86.

Therefore, the ventricular heart beat cycle begins with the ventricular paced event 15, which causes a contraction of the ventricles as indicated by the Q-wave 81. After a brief electromechanical delay, 85, the SCG wave from 14 shows the MC event 92. The time interval from mitral valve closure as indicated by MC event 92 and the opening of the aortic valve as indicated by AO event 94 is an isometric contraction phase contained in the pre-ejection period shown as PEP 24 in FIG. 1. The systolic phase of the heart extends from the MC event 92 to the AC event, which indicates aortic valve closure.

The conclusion of the systole and the beginning of the diastole is reflected by the aortic valve closure point indicated by AC event 97, and this phase of the heart cycle extends to the next mitral valve closure point indicated as MC event 84.

Identification of these wave form features is done based upon slope and amplitude information. The preferred deci sion rules applied to the representative wave forms are set forth as follow:

The MC event is the first peak occurring in time after the peak of the ECG R-wave;
The AO event is the first valley after the MC;
The RE event is the next peak after the AO;
The AC event is the first peak after the end of the ECG T-wave;
The MO event point is taken as the second valley following the AC event;
The RF event is the next peak after the MO; and
The AS event is taken as the last peak before the onset of the Q-wave in the ECG. It should be noted that T-waves are notoriously hard to locate due to the slow slope and low amplitude. In the absence of successful T-wave detection based upon slope information, the approximate T-wave position is defined based on measured QRS to QRS interval and the corresponding AC location is interpolated and defined as a result.

In process 65, time intervals are computed based upon the identified points. For example, the time interval 24 between the MC event 92 and the AO event 94 is measured and defined as the pre-ejection period. The time interval between the AO event 94 and the AC event 97 is measured and taken as the left ventricular ejection time. The specific interval measured relate to the specific index of cardiac performance that is selected for optimization.

In process 66, the preferred index of cardiac performance is the ratio of the pre-ejection period (PEP) to the left ventricular ejection time (LVET), which may be expressed as (PEP/LVET). For example, the maximum cardiac output at any given heart rate is maximized by the A-V delay interval which minimizes the ratio of the pre-ejection period to the left ventricular ejection time and optimization of this ratio is desirable. It appears that the maximization of the LVET is more important than minimization of PEP for most pacemaker patients. Similarly, other indexes of cardiac performance can be defined including: ((Q to MC)/LVET) and ((VP to MC)/LVET). These non-traditional measures may be better indicators of cardiac performance for some pacemaker patients.

These ratios involve pacing events that are readily detected and include electrical and electromechanical delay components. It should be recognized that the normal sinus depolarization of the heart has a different activation sequence than a paced beat, and measured PEP may vary between paced and sinus beats. For this reason, it may be preferable to optimize A-V delay based upon one of these non-traditional indices of cardiac performance. Consequently, although the preferred ratio of PEP to LVET is described in detail, the methods of the present invention may be extended to these and other non-traditional indices of cardiac performance.

In process 67, the lead placement and pacemaker settings that result in optimal resynchronization are determined. To provide a method for screening CRT candidates, SCG data is acquired from patients who have benefitted from CRT and compared to data from those who have not. For placement of pacemaker leads, the physician looks for an optimum location of leads, e.g., one that gives a global minimum for the ratios of PEP/LVET. Other parameters may be discovered during electrophysiological studies that are better indicators of CRT success for certain patients.

FIG. 4 is broken into panels that represent hard copy output 45 from printer 44. The upper panel 70 represents the canonical SCG and ECG waveforms annotated with SCG and ECG event locations. The table 72 of FIG. 4 shows the A-V delay intervals set and the corresponding time interval measurements along with computed ratios.

Process 67 selects the minimum value for the ratio of PEP/LVET and places the asterisk 74 in the table 72 to indicate the global minimum. This value can be considered by the physician and programmed into the pacemaker via the pacemaker programmer 41, or the value can be automatically selected and transmitted to the pacemaker programmer 41 via data link 30, to automatically program the pacemaker 35 to this value.

Figure 5:
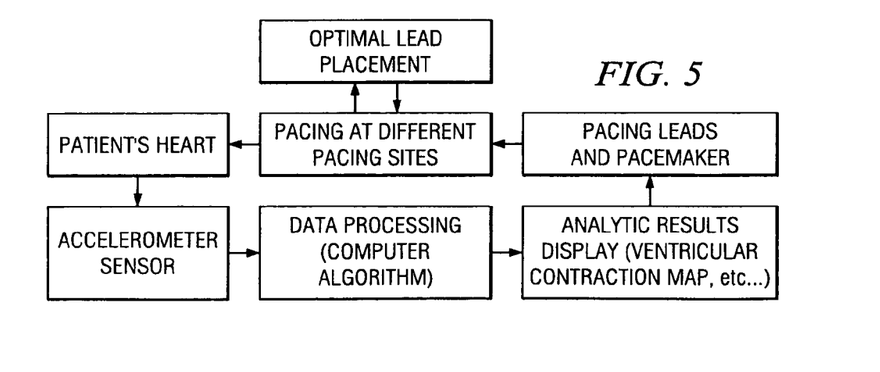
FIG. 5 is a block diagram showing in outline the optimal lead placement method for cardiac resynchronization therapy.

FIG. 5 schematically illustrates the optimal lead placement method for cardiac resynchronization. The system that accomplishes the method of the invention consists of the following components: an accelerometer sensor, pacing leads and a programmable electrical simulator (pacemaker), a computer analysis module, which includes unique algorithm that calculates numerous parameters during the cardiac cycle (including but not limited to duration of presystolic period, duration and pattern of ventricular ejection and diastolic relaxation period), and a computerized 2D and 3D display which includes ventricular contraction mapping that represents details of ventricular contraction.

The pacing leads are generally first placed at the right ventricular apex and left ventricular posterior or lateral wall through the coronary sinus. Next, a seismographic signal is obtained from an accelerometer that is placed on the chest of a patient and is processed by a computer algorithm. The results of this seismographic signal is analyzed and displayed as a ventricular contraction map with multiple parameters including the pre-ejection period, the duration of systole and the duration of isometric diastolic period as well as other parameters. Comparing these hemodynamic parameters during pacing with those during non-pacing (as well as at different pacing sites) will enable the physician to determine the best pacing site(s) and to screen candidates for CRT.

The present invention should provide data at the time of the pacing implant procedure to achieve the best resynchronization for left or biventricular pacing therapy. Numerous studies have reported that most patients with congestive heart failure, who have left bundle brunch block and QRS duration of greater than 130 ms, can be markedly improved by CRT accomplished by left ventricular or biventricular pacing. In addition, the selection of patients who would benefit and the results of the procedure should be greatly improved if the best pacing site(s) could be determined at the time of implantation. If it is found that synchronization therapy will also provide therapeutic benefit for patients with right bundle branch block, this invention could also be applied to these patients.

Three recently published reviews provide background information about resynchronization therapy for the treatment of congestive heart failure in a select group of patients. Dr. William Abraham in "Reviews of Clinical trails and Criteria for Identifying the Appropriate Patient," 2003 Vol. 4 (Supplement 2): S30–S37 reviewed the clinical trials that evaluated this treatment for heart failure. A total of 12 clinical trials has been completed or is still enrolling patients. The criteria for enrollment are generally patients who are in New York Heart Association function class 2–4 congestive heart failure, who have a QRS duration of greater than or equal to 120 ms (normal less than 100 ms), and who are in sinus rhythm. Most patients suffer from intraventricular conduction delay or left bundle branch block. Relatively few patients evaluated for this therapy are in atrial fibrillation or have right bundle branch block. These studies have shown the results of cardiac resynchronization therapy include an improvement of quality of life score, an increase in functional class, an increase in distance walked in six minutes, and an increase in peak oxygen consumption during exercise. Furthermore, one trial, "the Companion Trial", was powered and did show a decrease in all cause mortality and hospitalization.

However, most studies have shown that approximately 30% of patients identified by the above criteria do not obtain any measurable benefit from this therapy. Therefore, this represents a challenge. The lack of benefit may be due to lack of precision in selection criteria and/or lack of identification of the optimal pacing site or sites. A review by David A Cass "Ventricular Resynchronization: Pathophysiology and Identification of Responders" in "Reviews in Cardiovascular Medicine" 2003: Vol. 4 (Supplement 2: S3–S13) noted that QRS duration does not consistently narrow after biventricular pacing with many subjects displaying no change or even widening of the QRS duration.

Thus, QRS duration is at best an indirect correlation of mechanical desynchronization which is the real substrate that causes a decline in chamber function. Therefore, data have confirmed the initial results showing a general correlation between the basal QRS duration with efficacy of biventricular pacing but with a poor predictive value for identifying responders versus non-responders. The ability to predict responders is not yet clear. However, among the factors that are being considered and evaluated primarily by echocardiography include the interventricular dyssynchrony, the intraventricular dyssynchrony, successful lead placement, adequate pre-excitation, and physiological atrial-ventricular delay. Cass reviewed the data in the literature that show that a greater than 22% improvement in the maximum rise in left ventricular pressure (dp/dt max) acutely has been associated with consistent responders with few false negatives. Intraventricular delay appears to be more important than interventricular delay for defining responders. Intraventricular conduction delay may cause mechanical dispersion of motion between the septal and lateral walls. The most common means of detecting this is by echocardiography. Various techniques using echocardiography have been utilized including M-mode echo imaging and various tissue Doppler imaging techniques to detect and quantitate dyssynchrony. Although these techniques may be useful in helping to identify patients who may benefit from cardiac resynchronization therapy, these techniques have not been evaluated on a large scale to assess the percentage of patients who will benefit from cardiac resynchronization therapy.

In addition, echo evaluation is difficult if not impractical to assess the site of optimal lead placement at the time of the procedure for inserting the leads. As noted in the Review article by Sulukhe T. B., Henein N.Y. and Surton R. "Pacing and Heart Failure: Patient and Pacing Mode Selection, European Heart Journal 2003, Vol. 24 pp. 977–986, the aim of the biventricular pacing or ventricular resynchronization therapy is to optimize segmental electrical excitation, timing of contraction, relaxation and consequently cycle efficiency and that is the aim of the present invention. Sulukhe et al. reviewed data from a retrospective study that attempted to identify predictors of responders to biventricular pacing. There was no significant difference between the left ventricular lead position sites between the responders and the non-responders, but there was a trend toward a greater number of lateral and anterior left ventricular sites in patients whose symptoms and exercise tolerance improved.

Nevertheless, there has not been a study in which the optimal pacing sites have been compared at the time of implantation since there has not been a practical way of identifying optimal resynchronization at the time of the implant procedure. It is recognized that there are technical difficulties in positioning the pacing lead in the left ventricle by the coronary vein sine optimal sites may not always be accessible and are limited by venous anatomy by current lead placement technology. However, there are recent advances in lead placement technology including over-the-wire techniques and other methods that may permit greater flexibility in positioning the coronary sinus lead.

Once again, an aim of the current invention is to obtain patterns of chest wall motion that reflect cardiac desynchronization to help select patients who may benefit from this procedure and, at the time of lead placement, to identify the optimal lead site that will accomplish this. Data that will also be collected to help identify the effect of different AV delays on identifying optimal patters of optimal cardiac efficiency and output. These and other parameters can be assessed, including changes in the interventricular conduction delay. Additional parameters that can be assessed by the present invention are the duration of the pre-ejection period, the possible presence of mitral regurgitation as it affects the pre-ejection period, the rate of rise of the left ventricular ejection as determined by the accelerometer, the duration of systole, the rate of decrease of deceleration after peak acceleration and peak systole, the duration of systole, and the duration diastole.

Various changes in the details and components that have been described may be made by those skilled in the art within the principles and scope of the invention described in the specification and defined in the appended claims. Therefore, while the present invention has been shown and described herein in what is believed to be the most practical and preferred embodiments, it is recognized that departures can be made within the scope of the invention, which is not to be limited to the details disclosed herein but is to be accorded the full scope of the claims so as to embrace all equivalent processes and products.

We claim:

1. A method for determining the effectiveness of cardiac resynchronization therapy while stimulating a patient's heart at different locations during an electrophysiology study, comprising the steps of:
   (a) collecting seismocardiographic (SCG) data corresponding to heart motion during paced beats of said patient's heart;
   (b) collecting seismocardiographic (SCG) data corresponding to heart motion during un-paced beats of said patient's heart;
   (c) determining hemodynamic and electrophysiological parameters based on the SCG data of steps (a) and (b); and
   (d) determining whether cardiac performance is improved by comparing said hemodynamic and electrophysiological parameters generated by step (a) with those generated by step (b).

2. The method of claim 1, wherein the SCG data of steps (a) and (b) are detected by an accelerometer.

3. The method of claim 1, wherein said hemodynamic and electrophysiological parameters of step (c) are selected from the group consisting of one or more of the following: a pre-ejection period, a rate of contraction of left ventricle, a duration of systole, a duration of an isovolumic relaxation period, a rate of change of ventricular pressure, and an ejection fraction.

4. The method of claim 3, wherein the pre-ejection period is determined from a ventricular contraction mapping.

5. The method of claim 3, wherein the rate of contraction of left ventricle is determined from a ventricular contraction mapping.

6. The method of claim 3, wherein the duration of systole is determined from a ventricular contraction mapping.

7. The method of claim 3, wherein the duration of isovolumic relaxation period is determined from a ventricular contraction mapping.

8. The method of claim 1, wherein a ventricular contraction mapping is generated from the SCG data collected in steps (a) and (b).

9. The method of claim 8, wherein the a rate of change of ventricular pressure is determined from a ventricular contraction mapping.

10. The method of claim 1, further including the step of
    (e) determining whether left ventricular or biventricular pacing is more beneficial to said patient by comparing said hemodynamic and electrophysiological parameters generated by step (a) with those generated by step (b).

11. A method for selecting an optimal placement of leads of a cardiac pacing device for cardiac resynchronization therapy during implantation comprising the steps of:
    (a) selecting a lead placement location to place a lead of said cardiac pacing device;
    (b) collecting seismocardiographic (SCG) data corresponding to heart motion during paced beats of a patient's heart;
    (c) determining hemodynamic and electrophysiological parameters based on the SCG data of step (b);
    (d) repeating steps (a)–(c) for other lead placement locations for said cardiac pacing device; and
    (e) selecting a lead placement location that provides a best cardiac performance by comparing said hemodynamic and electrophysiological parameters of step (c) for each different lead placement location.

12. The method of claim 11, wherein the SCG data of step (b) are detected by an accelerometer.

13. The method of claim 11, wherein said hemodynamic and electrophysiological parameters of step (c) are selected from the group consisting of one or more of the following: a pre-ejection period, a rate of contraction of left ventricle, a duration of systole, a duration of an isovolumic relaxation period, a rate of change of ventricular pressure, and an ejection fraction.

14. The method of claim 13, wherein the rate of contraction of left ventricle is determined from a ventricular contraction mapping.

15. The method of claim 13, wherein the duration of systole is determined from a ventricular contraction mapping.

16. The method of claim 13, wherein the duration of isovolumic relaxation period is determined from a ventricular contraction mapping.

17. The method of claim 13, wherein the a rate of change of ventricular pressure is determined from a ventricular contraction mapping.

18. The method of claim 11, wherein a ventricular contraction mapping is generated from the SCG data collected in step (b).

19. The method of claim 13, wherein the prejection period is determined from a ventricular contraction mapping.

20. A system that selects an optimal placement of leads of a cardiac pacing device for cardiac resynchronization therapy during implantation, comprising:
    a cardiac pacing device with leads implanted into a patient's heart;

means for collecting seismocardiographic (SCG) data corresponding to heart motion during paced beats of said patient's heart;
means for determining hemodynamic and electrophysiological parameters based on said SCG data; and
a processing device that compares said hemodynamic and electrophysiological parameters;
wherein the optimal placement of leads of said cardiac pacing device is determined by comparing said hemodynamic and electrophysiological parameters for different lead placement locations.

21. The apparatus of claim 20, wherein said means for collecting SCG data comprises an accelerometer.

22. The system of claim 20, wherein said hemodynamic parameters are selected from the group consisting of one or more of the following: a pre-ejection period, a rate of contraction of left ventricle, a duration of systole, a duration of an isovolumic relaxation period, a rate of change of ventricular pressure, and an ejection fraction.

23. The system of claim 20, wherein a ventricular contraction mapping is generated from the SCG data.

* * * * *